(12) United States Patent
Nacson

(10) Patent No.: US 9,329,156 B2
(45) Date of Patent: *May 3, 2016

(54) AIRCRAFT SCREENING DEVICE AND METHOD

(71) Applicant: Teknoscan Systems, Inc., Vaughan (CA)

(72) Inventor: Sabatino Nacson, Thornhill (CA)

(73) Assignee: Teknoscan Systems, Inc., Vaughan, Ontario (CA)

( * ) Notice: Subject to any disclaimer, the term of this patent is extended or adjusted under 35 U.S.C. 154(b) by 647 days.

This patent is subject to a terminal disclaimer.

(21) Appl. No.: 13/685,089

(22) Filed: Nov. 26, 2012

(65) Prior Publication Data

US 2013/0137183 A1 May 30, 2013

Related U.S. Application Data

(60) Provisional application No. 61/565,471, filed on Nov. 30, 2011.

(51) Int. Cl.
*G01N 30/00* (2006.01)
*G01N 1/22* (2006.01)
*G01N 1/40* (2006.01)
*G01N 1/02* (2006.01)

(52) U.S. Cl.
CPC ............... *G01N 30/00* (2013.01); *G01N 1/2214* (2013.01); *G01N 2001/022* (2013.01); *G01N 2001/024* (2013.01); *Y10T 436/141111* (2015.01); *Y10T 436/142222* (2015.01); *Y10T 436/173845* (2015.01)

(58) Field of Classification Search
CPC ............... G01N 30/00; G01N 1/2214; G01N 2001/022; G01N 2001/024; Y10T 436/142222; Y10T 436/141111; Y10T 436/173845
See application file for complete search history.

(56) References Cited

U.S. PATENT DOCUMENTS

| | | | |
|---|---|---|---|
| 4,718,268 A | 1/1988 | Reid et al. | |
| 4,866,439 A | 9/1989 | Krause | |
| 5,274,356 A | 12/1993 | Taricco | |
| 5,395,589 A | 3/1995 | Nacson | |
| 5,859,375 A | 1/1999 | Danylewych-May et al. | |
| 6,690,005 B2 | 2/2004 | Jenkins et al. | |
| 7,299,710 B2 | 11/2007 | Syage | |
| 8,206,475 B2 * | 6/2012 | Walkinshaw | 55/385.2 |
| 8,220,312 B2 * | 7/2012 | Nacson | 73/31.01 |
| 2002/0148305 A1 | 10/2002 | Danylewych-May et al. | |
| 2007/0137319 A1 | 6/2007 | Nacson | |
| 2009/0084201 A1 * | 4/2009 | Almirall et al. | 73/864.81 |

(Continued)

OTHER PUBLICATIONS

McCaffrey et al. "A Model Study of the Aircraft Cabin Environment Resulting from In-Flight Fires." FAA Report, 1992.*

(Continued)

*Primary Examiner* — Christopher A. Hixson
(74) *Attorney, Agent, or Firm* — Kagan Binder, PLLC

(57) ABSTRACT

A method of screening aircraft passengers and/or cargo comprising loading an aircraft with passengers, cargo or both, circulating air within the aircraft so that the air is in contact with the passengers and/or cargo, expelling some of the circulated air from the aircraft, diverting a portion of the air being expelled from the aircraft through a chemical filter configured to retained evidence of a target substance, and analyzing the chemical filter to detect the presence of a target substance within the aircraft.

6 Claims, 7 Drawing Sheets

(56) References Cited

U.S. PATENT DOCUMENTS

2010/0326216 A1* 12/2010 Nacson .................. 73/864.35
2011/0015875 A1* 1/2011 Walte et al. .................. 702/24

OTHER PUBLICATIONS

Nyden, Marc R. "A Technical Assessment of Portable Explosives Vapor Detection Devices." National Institute of Justice Report, 1990.*

* cited by examiner

AIRCRAFT SCREENING DEVICE AND METHOD

PRIORITY

This non provisional application claims the benefit of provisional application having Ser. No. 61/565,471, filed on Nov. 30, 2011, and entitled "DETECTOR AND METHOD OF DETECTION," which application is incorporated herein by reference in its entirety.

FIELD OF THE INVENTION

The present invention relates generally to the detection of prohibited goods, and more particularly to a method and system for screening aircraft passengers and/or air cargo for prohibited substances.

BACKGROUND OF THE INVENTION

Air passengers and air freight (aircraft cargo) are often screened before an aircraft is loaded. The object of pre-flight screening is to detect prohibited goods and prevent them being loaded onto an aircraft.

Screening generally takes place at the airport where the aircraft is scheduled to depart. Passengers are screened by specially trained airport staff (or sometimes police) in a segregated area prior to departure gates. Air freight is also screened within the airport. Some forms of screening may also be undertaken at the destination airport (such as narcotic screening).

Specific forms of screening include inspection by purpose trained dogs ('sniffer' dogs), physical searches, metal detection scanning, passenger imaging (including controversial whole body scanning), cargo content imaging and surface testing for the presence of explosive residue.

Various forms of screening may be employed by airport authorities. Some forms of screening may be used by authorities to target specific prohibited goods. As a result, passenger and/or cargo may endure several stages of screening and different screening techniques before entering the aircraft. In some instances suspect passengers or cargo may be identified for additional screening.

Some prohibited goods that may be the subject of pre-flight screening include weapons or potential weapons (such as sharp objects, firearms or explosives), flammable goods (such as matches, lighters and flammable fluids), animals (particularly endangered specifies), narcotics, chemical warfare agents, biological warfare agents, nuclear or radiological agents, ammunitions, toxic industrial chemicals or waste, embargoed or smuggled items (such as tobacco) and explosives or other volatiles.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

The following presents a simplified summary of the disclosure in order to provide a basic understanding to the reader. This summary is not an extensive overview of the disclosure and it does not necessarily identify key/critical elements of the invention or delineate the scope of the invention. Its sole purpose is to present some concepts disclosed herein in a simplified form as a prelude to the more detailed description that is presented later.

The present invention provides a method of screening aircraft passengers and/or cargo comprising:
loading an aircraft with passengers, cargo or both,
circulating air within the aircraft so that the air is in contact with the passengers and/or cargo,
expelling some of the circulated air from the aircraft,
diverting a portion of the air being expelled from the aircraft through a chemical filter configured to retained evidence of a target substance, and
analyzing the chemical filter to detect the presence of a target substance within the aircraft.

The air may be circulated by activating an onboard air circulation system within the aircraft. The expelled air may be diverted from the outlet of an onboard air circulation system located on the exterior of a aircraft. The method may comprise the further step of selecting a sampler probe based on the volume flow rate of air being expelled from the aircraft. The samples may be taken from the expelled air for about 5 minutes to about 30 minutes depending on how long the passengers, cargo or both have been on the aircraft. The air may be diverted through the chemical filter at a flow rate in excess of 1000 L/min.

The filter may comprise a coating configured to absorb/adsorb the one or more target substances, the coating comprising materials being selected from the group consisting of diphenylene oxide polymers prepared in chloroform, a carbon composite material, divinyl benzene, mono-alkyl substituted benzenes, di-alkyl substituted benzene, toluene, xylenes, ethylbenzene and silicone oils with high thermal stability and boiling points. The coating materials may include diphenylene oxide polymers prepared in chloroform. The coating materials may include a carbon composite material. The carbon composite material may be graphite. The carbon composite material may be fullerenes. The carbon composite material may be polymeric carbons from soot produced from nitro substituted alkylbenzenes. The coating materials may include divinyl benzene. The coating materials may include mono-alkyl substituted benzenes. The coating materials may include di-alkyl substituted benzene. The coating materials may include toluene. The coating materials may include xylenes. The coating materials may include ethylbenzene. The coating materials may include silicone oils with high thermal stability and boiling points. The coating materials may include at least two materials selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The coating materials may include at least three materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The coating materials may include at least four materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene.

The expelled air from the aircraft may be diverted through the chemical filter for a continuous period of sufficient duration to span an aircraft entire air exchange.

The target substance may be a narcotic (such as cocaine, heroin, amphetamines, methamphetamines, THC) or an explosive.

The method may further comprise taking air samples for the entire aircraft, including passenger overhead luggage compartments, seats, storage luggage area, cargo areas and ULD containers.

The expelled air from the aircraft may constitute a sample of the entire aircraft, including passenger overhead luggage compartments, seats, storage luggage area, cargo areas and ULD containers.

The present invention further provides a method of screening aircraft passengers and/or cargo comprising:
loading an aircraft with passengers, cargo or both,
circulating air within the aircraft so that the air is in contact with the passengers and/or cargo,
expelling some of the circulated air from the aircraft,
sampling a portion of the air expelled from within the aircraft, and
analyzing samples collected from the expelled air to detect the presence of prohibited substances within the aircraft.

In this method, the air may be circulated by activating an onboard air circulation system within the aircraft. The sampling may be conducted outside the aircraft at the outlet of an onboard air circulation system. The method of may comprise the further step of selecting a sampler probe based on the volume flow rate of gases being expelled from the aircraft. The samples may be taken from the expelled air for about 10 minutes to about 30 minutes depending on how long the passengers, cargo or both have been on the aircraft. The sampling may be conducted at a flow rate in excess of 1000 L/min. A sampler probe may be used to divert a portion of the air expelled from the aircraft over a filter, the filter being configured to retained evidence of a target substance in the expelled air. The filter may comprise a coating configured to absorb/adsorb the one or more target substances, and the coating may comprise materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The coating materials may include silicone oils with high thermal stability and boiling points. The coating materials may include at least two materials selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The coating materials may include at least three materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The coating materials may include at least four materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The sampling may occur for a continuous period of sufficient duration to span an aircraft entire air exchange. The prohibited substances may include narcotics (such as cocaine, heroin, amphetamines, methamphetamines, THC) or explosives. The method may further comprise sampling the entire aircraft, including passenger overhead luggage compartments, seats, storage luggage area, cargo areas and ULD containers. The expelled air from the aircraft may constitute a sample of the entire aircraft, including passenger overhead luggage compartments, seats, storage luggage area, cargo areas and ULD containers.

The present invention further provides a system for screening aircraft passengers and/or cargo comprising:
a sampling probe,
a sampling card comprising a substrate coated with a filtering materials, the filtering materials being configured to retain vapors and/or particles of a target substance,
a sampler housing configured to house the sampler card,
wherein the sampling probe is configured to divert a portion of the air expelled from an aircraft air circulation system through the sampling housing so that the sampling card is exposed to the diverted air.

In this system, the filtering materials may be configured to absorb/adsorb the one or more target substances, and the filtering materials may be selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The filtering materials may include at least two materials selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The coating materials may include at least three materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene. The coating materials may include at least four materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene.

The present invention further provides a method of screening aircraft passengers and passenger luggage comprising:
i. loading passenger luggage into an air freight container, drawing a sample from the container using suction before the container is loaded into an aircraft, passing the sample through a chemical filter configured to retained evidence of a target substance in the sample, and analyzing the chemical filter to detect the presence of a target substance within the container,
ii. drawing a sample from a passengers clothing or hand luggage using suction prior to the passenger boarding an aircraft, passing the sample through a chemical filter configured to retained evidence of a target substance, and analyzing the chemical filter to detect the presence of a target substance on the passengers clothing or hand luggage, and
iii. loading an aircraft with passengers and luggage containers, circulating air within the aircraft so that the air is in contact with the passengers, expelling some of the circulated air from the aircraft, diverting a portion of the air being expelled from the aircraft through a chemical filter configured to retained evidence of a target substance, and analyzing the chemical filter to detect the presence of a target substance within the aircraft.

The present invention further provides a method of screening aircraft passengers comprising:
unloading aircraft passengers from an aircraft,
using a portable sampler to draw a sample from within the aircraft,
passing the sample through a chemical filter configured to retained evidence of a target substance, and
analyzing the chemical filter to detect the presence of a target substance within the aircraft.

In this method, the sample may be drawn from a passenger seat or an overhead locker space where carry-on luggage is stored during flight. The passengers may be unloaded from the aircraft after the aircraft has landed at the completion of a journey.

The present invention further provides a method of screening aircraft passengers and/or cargo comprising:
- unloading passengers and/or cargo from an aircraft at the completion of a journey,
- circulating air within the aircraft,
- expelling some of the circulated air from the aircraft,
- diverting a portion of the air being expelled from the aircraft through a chemical filter configured to retained evidence of a target substance, and
- analyzing the chemical filter to detect the presence of a target substance within the aircraft.

The present invention further provides a portable sampler comprising:
- a vacuum pump,
- an inlet coupled to the vacuum pump so that activation of the vacuum pump creates suction at the inlet,
- a filter housing disposed between the inlet and the vacuum pump, the filter housing capable of receiving filters of different configurations.

The blower port may be coupled to a discharge port of the vacuum pump, and the blower port may be configured to discharge gases across a target to stir the air.

DETAILED DESCRIPTION OF THE INVENTION

Aircraft security and narcotics detection have become significant objectives for international and domestic airports. Passengers and cargo are often extensively screened prior to being loaded on aircraft. Screening processes can take a significant amount of time, require advanced expertise and inconvenience passengers.

Security screening is predominantly concerned with detecting concealed weapons. Explosives and other volatile substances are a particular concern in the aviation industry. Screening for possible explosives can be an involved process without guaranteed results. Narcotic screening is similarly involved.

Post Loading Aircraft Screening

Explosives, highly flammable substances and certain narcotic constituents are often volatile at room temperature, dispersing trace quantities of vapor into the surrounding environment, even when concealed. Residue from explosives substances and narcotics can also be difficult to remove from surfaces they have been in contact with, which may also contribute to an environmental trace presence. Trace particulates may also be present in the environment surrounding explosives and narcotics if the substances have been recently disturbed.

Post-loading analysis of the environment within an aircraft may be used as a screening method to detect explosives (both volatile and non-volatile), flammable substances and narcotics (such as cocaine, heroin, amphetamines, methamphetamines, and THC). Environmental analysis may also detect other prohibited goods.

One method of screening aircraft passengers and/or cargo comprises loading the aircraft (with passengers, cargo or both), circulating air within the aircraft so that the air is in contact with the passengers and/or cargo, expelling some of the circulated air from the aircraft, sampling a portion of the air expelled from within the aircraft, and analyzing samples collected from the expelled air to detect the presence of a target substance or a prohibited substances within the aircraft. The sample may be taken by diverting a portion of the air being expelled from the aircraft through a chemical filter configured to retain evidence of a target substance.

Generally, an onboard air circulation system (such as an air-conditioning system) can be used to circulate air within the aircraft. Aircraft air circulation systems are commonly activated before passengers are loaded onto the aircraft or soon thereafter. Samples may then be collected outside the aircraft at the outlet of the onboard air circulation system.

Air is commonly expelled from the aircraft at a high volume flow rate (a large commercial aircraft may exhaust around 245 m$^3$/hr of air while cruising, and at about 350 m$^3$/hr while on the ground). Although only a portion of the expelled air is sampled, the volume flow rate across the filter may still exceed 1000 L/min (60 m$^3$/hr).

Figure 1:
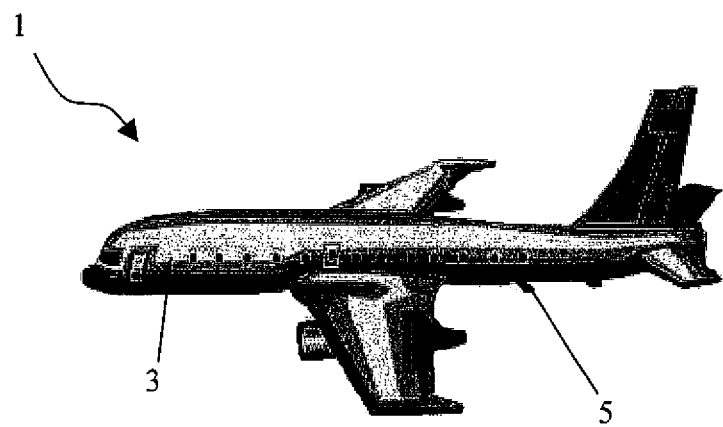
FIG. 1 is a perspective view of an aircraft.
Figure 2:
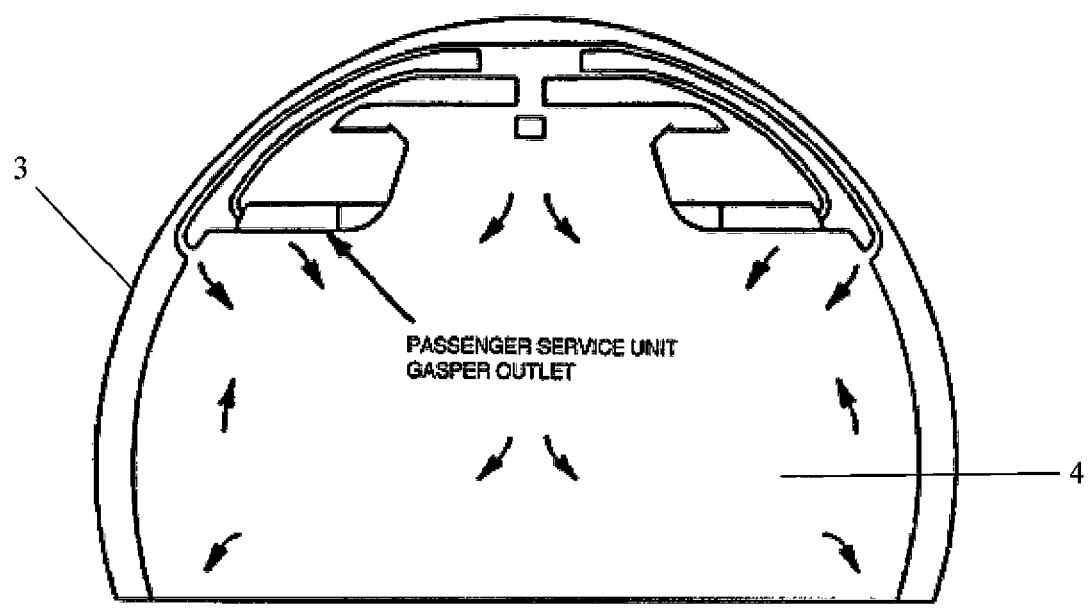
FIG. 2 is a schematic representation of air circulation within an airplane cabin about a cross section transverse to the fuselage (i.e. wing to wing).

One type of aircraft 1 is illustrated in FIG. 1. The outlet 5 of the aircraft air circulation system is shown toward the rear of the aircraft 1 on the underside of the fuselage 3. The illustrated outlet 5 is a dump valve. The dump valve releases air from the air circulation system to the aircraft surroundings.

The sampling process generally involves diverting a portion of the expelled air over a purpose-designed chemical filter. The filter retains particular constituents of the diverted air. The constitution of the filter medium is generally selected to target particular substances, and multiple filters may be employed to collect a broad sample spectrum.

The sampling duration generally varies from about 2 minutes to about 30 minutes, but can usually be performed in about 10 minutes depending on the specifications of the aircraft being sampled. The actual sample time for each screening reflects the length of time the passengers and/or cargo have been on the aircraft, how long the air circulation system has been active and the air exchange rate of the particular aircraft (the time to completely replace air within the aircraft with air from the surrounding environment). The sampling duration is calculated (or otherwise determined) to provide sufficient time for substance traces to collect within the filter and ensure adequate statistical verification of the sample. Ideally, sampling spans at least an entire air exchange to allow adequate trace accumulation.

The sample may be rapidly analyzed once the sampling period has expired. Analysis times between about 90 seconds and 180 seconds are possible. It is desirable to process the sample before the aircraft prepares for departure so that the aircraft may be grounded or re-sampled if there is any uncertainty.

Air Circulation System Sample Collection

Samples are collected from the outlet of the aircraft air circulation systems (commonly a dump valve). The samples may be collected by iso-kinetic sampling. Suction or other forms of aspiration may also be used to direct microscopic particles toward the filter and concentrate vapors.

The volume flow rate of air expelled from the aircraft is generally in the range of about 2 $m^3$/min to about 10 $m^3$/min, and may vary depending on the size and make of the aircraft and thermal loading on the air conditioning system (where applicable).

The maximum recommended volume flow rate across chemically coated sampling filters is generally limited to a range from about 1 $m^3$/min to about 2 $m^3$/min, significantly less than the volume flow rate expelled from most aircraft. The efficacy and/or efficiency of a sampling filter may be adversely affected by operating above the recommended operating flow rate as the filter collection efficiency will be reduced and vapor breakthrough is more likely to occur. The ability of the filter to trap the target substance(s) and provide a statistically viable sample will usually require adherence to defined operating conditions, which may include defined flow rates.

In general, the trapping efficiency of chemical filters is better at lower flow rates. Higher sample flow rates (such as above a filter flow rating) can cause vapor stripping from the filter coating and an inadequate residence time of target substances within the filter medium (reducing interaction with the active sites on the filter). Above the rated flow of the filter, the retention time of target substances can be reduced below acceptable levels and volatile chemicals may break through the thin film coating and avoid retention in the filter entirely.

Figures 3A, 3B, 3C:
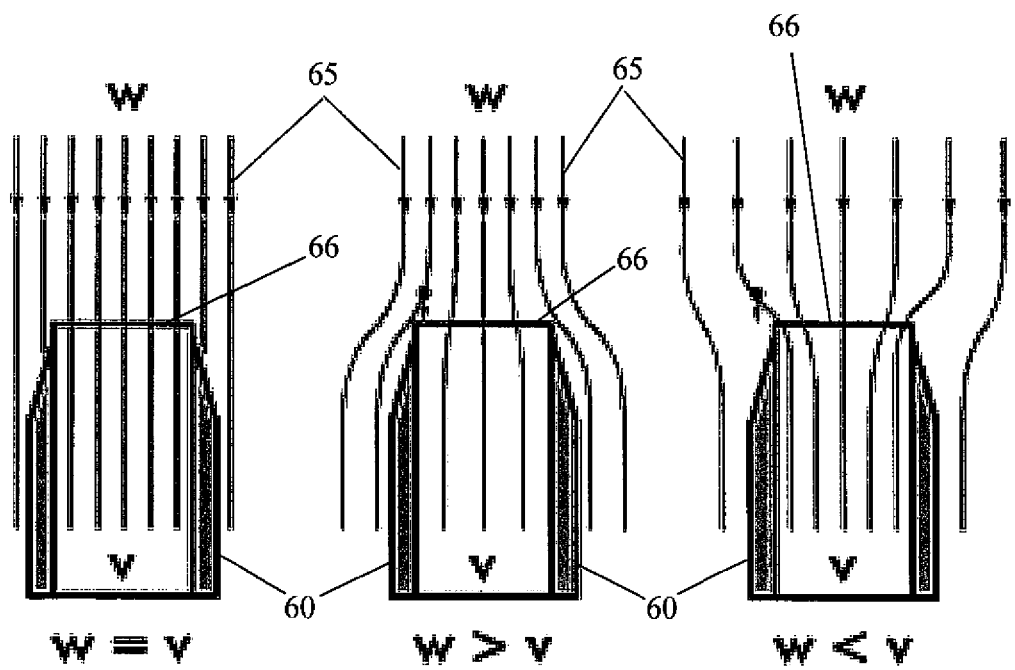
FIG. 3a is a schematic representation of airflow over a sampling probe where the probe velocity rating is matched to the expelled air velocity.
FIG. 3b is a schematic representation of airflow over a sampling probe where expelled air velocity is greater than the probe velocity rating.
FIG. 3c is a schematic representation of airflow over a sampling probe where expelled air velocity is less than the probe velocity rating.

A fluid collection probe 60 is illustrated in FIGS. 3a to 3c. The probe 60 is shown in the path of air being expelled from an aircraft air circulation system, with the longitudinal axis of the probe 60 generally aligned with the outlet flow. The flow path of the expelled air around and through the probe 60 is represented by a set of flow lines 65. The outlet flow rate (w) of expelled air (measures at the aircraft air circulation system outlet) varies in each representation. The illustrated probe 60 is rated for a specific range of flow rates (v). The rated flow rate (v) of the probe 60 is the same for FIGS. 3a to 3c.

FIG. 3a illustrates expelled air from the air circulation system travelling at a flow rate (w) within the range of rated flow rates (v) for the probe 60. There is minimal disturbance of the flow lines 65 around the probe 60.

FIG. 3b illustrates expelled air travelling at a flow rate (w) in excess of the rated probe 60 flow rate (v). The flow lines 65 diverge outwardly around the probe 60, creating angled flow across the opening of the probe 65.

FIG. 3c illustrates expelled air travelling at a flow rate (w) at a lower velocity than the rated probe 60 flow rate (v). The flow lines 65 converge inwardly of the probe 60, again creating angled flow across the probe 65 opening.

Flow deviations around the mouth 66 of the probe 60, as illustrated in FIGS. 3b and 3c, are undesirable as they can lead to inefficient sampling and drive minute particles away from the probe 60. Ideally, the probe 60 is selected to match the flow rate of expelled air leaving the aircraft, as illustrated in FIG. 3a. Adequately matching the probe 60 to the outlet flow allows a broad range of particles to be collected in the target range (1-100 μm). The probe 60 may be fitted with a screen (not illustrated) to prevent debris from interfering with the filter.

Suitable sampler probes 60 may have an internal diameter generally in the range of about 3 mm to about 30 mm. The internal diameter of the probe may be selected to match the air circulation outflow characteristics of an aircraft. In general, greater internal probe diameters relate to higher probe flow ratings.

The characteristics of the target substance may also influence the selection of sampler probe 60. Intentionally mismatching the air flow rate and sampler probe flow rating (but not the sampler filter rating) can influence the collection of particles by altering the air flow patterns around the probe 60. In particular, larger particles may be driven away from the probe 60 by deviations in the air flow, allowing collection of smaller particles in the filter.

Aircraft Environmental Control System

Most passenger aircraft employ some form of environment control system (ECS) that regulates the atmosphere within the aircraft. An ECS will generally incorporate some form of air circulation system and may regulate various environmental parameters (such as temperature, pressure and humidity) within the aircraft. A high level block diagram graphically representing the various facets of an aircraft ECS is illustrated in FIG. 2. The ECS represented in FIG. 2 is responsible for pressurizing the aircraft, providing air conditioning and cooling any auxiliary equipment.

The ECS components are dispersed about the fuselage of an airplane. A cooling and circulation system is illustrated in mid way along the fuselage 3 (adjacent the wings).

The cooling and circulation system receives air from a ram air system. The ram air system inlets are disposed within the aircraft propulsion engines. The outlet of the cooling and circulation system is coupled to an air distribution network that extends about the airplane fuselage 3. The air distribution network circulates air within the aircraft cabin 4 when the ECS is active.

The aircraft ECS will generally circulate air about the entire aircraft (including passenger overhead luggage compartments, storage luggage areas, and the cargo areas amongst ULD containers). Where the ECS expels air through multiple outlets it may be necessary to obtain a sample from each outlet to ensure the entire aircraft is adequately sampled. The sampling procedure may be adjusted to reflect the characteristics of the aircraft being sampled and avoid sample bias. It is generally desirable to sample the entire aircraft, including passengers overhead luggage compartments, seats, storage luggage area, and cargo areas where the ULD containers are stored.

Typical ECS flow rates for a Boeing 757 are shown in Table 1 below.

TABLE 1

Typical ECS flow rates for a Boeing 757

| | Passenger cabin - Two packs with recirculation | | Two packs @ 165% | Pressure (psia) | | |
|---|---|---|---|---|---|---|
| Flight regime | Total (cfm) | Fresh air (cfm) | All fresh (cfm) | Pack outlet | Cabin supply | Ambient |
| Sea level | 3296 | 1714 | 2828 | 15.1 | 14.7 | 14.7 |
| 5,000 ft. climb | 3284 | 1740 | 2871 | 15.1 | 14.7 | 12.2 |
| 10,000 ft. climb | 3251 | 1690 | 2789 | 15.1 | 14.7 | 10.1 |

TABLE 1-continued Typical ECS flow rates for a Boeing 757

| | Passenger cabin - Two packs with recirculation | | Two packs @ 165% | Pressure (psia) | | |
|---|---|---|---|---|---|---|
| Flight regime | Total (cfm) | Fresh air (cfm) | All fresh (cfm) | Pack outlet | Cabin supply | Ambient |
| 25,000 ft. cruise | 3212 | 1638 | 2703 | 14.4 | 14.1 | 5.45 |
| 30,000 ft. cruise | 3250 | 1690 | 2789 | 13.3 | 12.9 | 4.36 |
| 35,000 ft. cruise | 3711 | 1670 | 2756 | 12.3 | 11.9 | 3.46 |
| 42,000 ft. cruise | 3645 | 1677 | 2767 | 11.3 | 10.9 | 2.48 |
| 20,000 ft. descend | 3682 | 1730 | 2855 | 14.1 | 13.7 | 6.75 |
| 10,000 ft. descend | 3645 | 1677 | 2767 | 14.8 | 14.3 | 10.11 |

A summary of aircraft environment control systems can be found in the following references: "Aircraft ventilation systems study", Lorengo and Porter (ASHRAE Research Project 978. Final Report. Institute for Environmental Research, Kansas State University, Manhattan, Kans., May 1, 2001); "Enhanced emergency smoke venting", Elliott L. Maylor (published by the U.S. Department of Transportation, Federal Aviation Administration, FAA Technical Center, 1988); "Airplane tests of enhanced emergency smoke venting," Elliott L. Maylor (published by the U.S. Department of Transportation, Federal Aviation Administration, FAA Technical Center, 1989); "Generation of a buoyant plume of artificial smoke for airplane tests", Thor I. Eklund (published by the U.S. Department of Transportation, Federal Aviation Administration, FAA Technical Center, 1990); "A model study of the aircraft cabin environment resulting from in-flight fires", B. J. McCaffrey (published by FAA Technical Center, U.S. Department of Transportation, Federal Aviation Administration, 1993); "An analysis for relating visibility to smoke production and ventilation", B. J. Eklund (technical report DOT/FAA/CT-TN84/22 published by the Fire Safety Branch of the Federal Aviation Administration, May 1984); and "Aircraft accident report, Air Canada flight 797, McDonnell Douglas DC-9-32, C-FTLU, Greater Cincinnati International Airport, Covington, Ky., Jun. 2, 1983", published by the U.S. National Transportation Safety Board.

Substance Retention and Analysis

Figure 4:
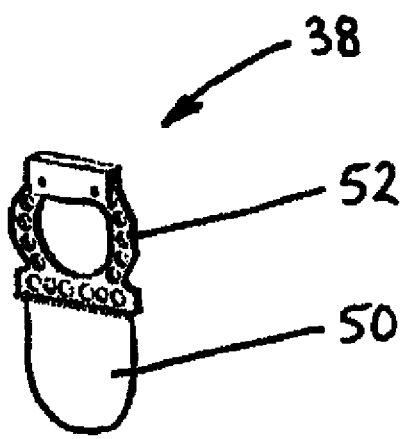
FIG. 4 is a perspective view of a sampler card.

A sampling card 38 is illustrated in FIG. 4. The sampling card 38 comprises a substrate 50 coated with a combination of adsorbent/absorbent materials. The adsorbent/absorbent materials function as a chemical filter, concentrating vapors and entrapping fine airborne particles when air is directed over the sampling card 38. A handle 52 is formed at one end of the substrate 50. The handle 52 facilitates handling of the sampling card 38, allowing the sampling card to be readily inserted into and removed from a suitable sampler.

The substrate 50 may be formed of a stainless steel mesh. Other possible substrate materials include nickel, copper, aluminum, fiberglass, porous Teflon, cotton, Nomex and other man-made fibers.

The combination of adsorbent/absorbent materials may comprises two or more of diphenylene oxide polymer(s) prepared in chloroform, carbon composite materials such as graphite, fullerenes, polymeric carbons from soot produced from nitro substituted alkylbenzenes, divinyl benzene, monoalkyl substituted benzenes, di-alkyl substituted benzene, toluene, xylenes, ethylbenzene, silicone oils with high thermal stability and boiling points and adsorption properties for wide range of organic compounds or other suitable materials, although silicone oils are not preferred The sampling card 38 is inserted into a sampler housing before being exposed to air from an aircraft air circulation system. The housing is specifically configured to moderate the flow rate through the sampling card 38. The card 38 and associated housing may be specifically configured for a particular aircraft or group of aircraft with similar air circulation characteristics.

Air entering the sampler housing is passed through the coated substrate 50 of the sampling card 38. Localized vapors and airborne particles within the sampled air are entrapped by the adsorbent/absorbent materials coating the sampling card substrate 50.

At the end of the predetermined sampling period, the sampling card 38 is removed from the housing and analyzed. Commonly, the concentrated or enriched sample retained within the card 38 is thermally desorbed into a detector system to enable analysis. This is achieved by heating the sampling card 38 to evaporate entrapped vapors and release entrapped particles.

An analyzer is then used to detect the presence of any prohibited substances. Some analyzers that may be used to evaluate the sample include chromatographic analyzers, mass spectrometers (stationary or portable), chemiluminescent detectors, axial ion mobility spectrometers (AIMS) and field asymmetric ion mobility spectrometry analyzers (FAIMS), which are also sometimes referred to as differential mobility spectrometers (DMS). Combination analyzers may also be used, such as fast gas chromatography, ion mobility spectrometer (GC-IMS), or GC-mass spectrometry, or a tandem combination of GC-IMS-MS Research indicates that the concentration of prohibited substances within the aircraft air sample is likely to be at a level of parts per trillion, and the size of airborne particles is likely to range from about 1 to about 100 μm.

The quantity of prohibited substances (Ns) retained within the sampling card 38 can be calculated from Equation 1.

$$N_s = E_T \times Q_s \times C_s \times t_s \quad \text{(Equation 1)}$$

where:

$N_s$ is the quantity of prohibited substance retained in sampling card 38 in ng $E_T$ is the trapping efficiency of the sampling card 38

$Q_s$ is the flow rate through the sampling card 38 mL/min $C_s$ is the concentration of prohibited substance in the aircraft in ng/L $t_s$ is the sampling time in minutes The substances retained within the sampling card 38 are often thermally desorbed for analysis. The desorbed substance concentration ($C_d$) can be evaluated from Equation 2.

$$C_d = E_D \times N_s / Q_d \times t_d \quad \text{(Equation 2)}$$

where:

$E_D$ is the efficiency of sample desorption $C_d$ is the concentration of prohibited substance desorbed from card 38 in ng/L $N_s$ is the quantity of prohibited substance in card 38 in ng $Q_d$ is the desorption gas flow rate in L/min $t_d$ is the desorption time in minutes Desorption temperature and flow rate govern the desorption profile of the substances evaporated from the card 38. These parameters can be tailored to accommodate different types of analyzer data acquisition and ionization sources.

The enrichment factor for volatile substances is defined by combining Equations 1 and 2 to arrive at Equation 3.

$$E_F = E_T \times Q_s \times t_s / Q_d \times t_d \quad \text{(Equation 3)}$$

Even at extremely low concentrations (on the order of parts per trillion) explosives can be detected. The typical detection limit of an IMS or MS system is around 100 picograms for some explosives.

Experimental results with a TNT vapor generator (using diluted concentration) when sampled with a high volume flow rate system were estimated at 10 pptv. Sampling was carried out for 30 seconds and the resulting data is shown in Table 2 below for seven consecutive runs on the vapor generator.

TABLE 2

Experimental sampling results with a TNT vapor generator

| Run # | Detector Signal (pA) | Equivalent amount (ng) | TNT concentration (pptv) |
|---|---|---|---|
| 1 | 139 | 1.0 | 0.22 |
| 2 | 163 | 1.1 | 0.24 |
| 3 | 120 | 0.8 | 0.18 |
| 4 | 146 | 1.0 | 0.22 |
| 5 | 156 | 1.1 | 0.24 |
| 6 | 137 | 0.9 | 0.18 |
| 7 | 176 | 1.2 | 0.26 |

TNT vapors were concentrated and held in the coating of the sampling card 38 and were not lost during sample collection under extreme flow rates. Low TNT vapor concentrations were collected and detected in the experiment.

Substance vapor concentrations are generally greater at or near the top of each aircraft compartment (e.g. vapors will generally concentrate in the headspace of the passenger cabin). Conversely, explosive particles are generally macroscopic (in the range of about 1 μm to about 100 μm) and can settle to the bottom of the respective compartments, given sufficient time. Particles greater than 10 μm generally become airborne and are captured in the circulation system.

Ideally, the aircraft air circulation system is activated before or soon after the aircraft is loaded so that macroscopic particles disturbed by the loading process do not settle within the aircraft.

Air Cargo Screening

Air freight (cargo or luggage) is commonly stored in "unit load devices" (ULDs) containers before being loaded into an aircraft. A ULD container is a specialized container that is usually purpose-built for a particular aircraft or group of aircraft. ULD containers are generally loaded with freight within the airport and subsequently loaded onto the aircraft. Conventionally, freight screening occurs before the cargo is loaded into a ULD container (or any other form of aircraft cargo container that may be used).

A method and system for screening ULD containers and other air freight containers is disclosed. ULD container screening involves sampling the air within the container and entrapping vapors and airborne particles on a treated card for subsequent analysis. The method allows the containers to be sampled after luggage and air cargo has been loaded without the need to reopen the containers.

Figure 5:
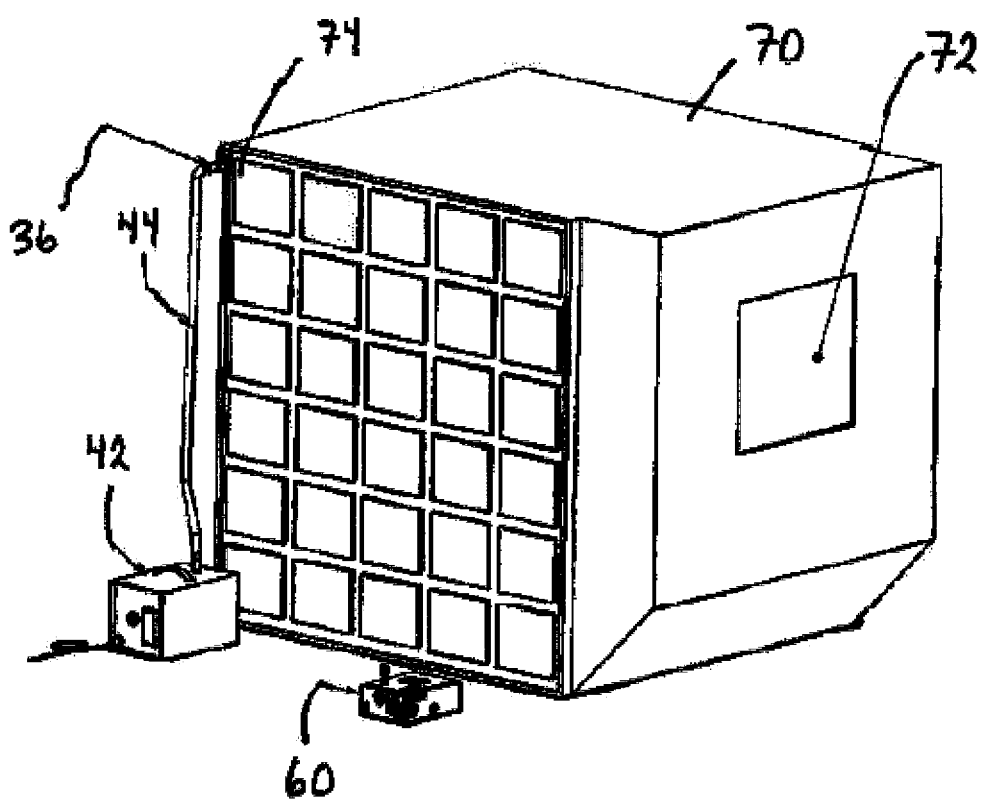
FIG. 5 is a perspective view of an air freight cargo container being screened.
Figure 6:
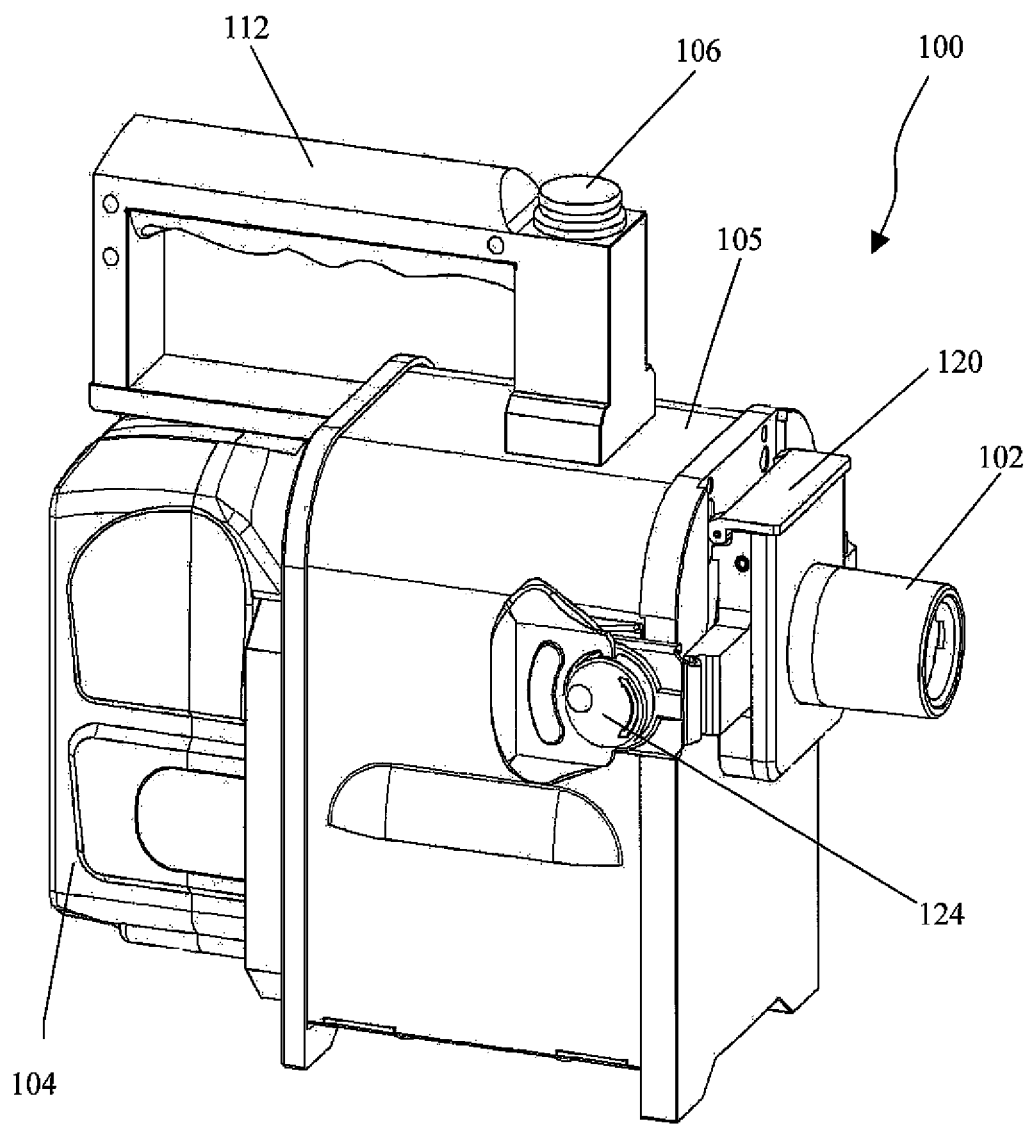
FIG. 6 is a perspective view of a handheld sampler illustrating the top, front and right side of the sampler.
Figure 7:
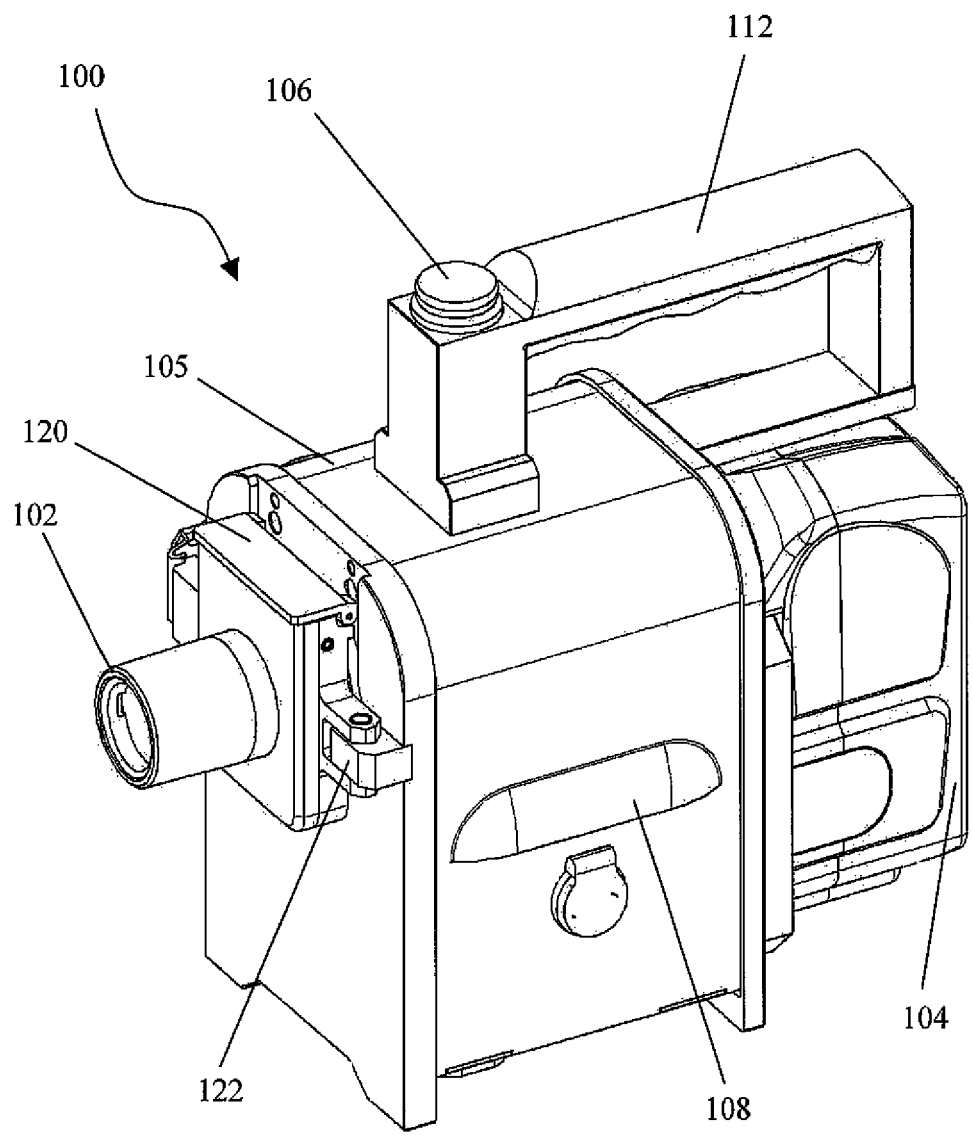
FIG. 7 is a perspective view of the handheld sampler of FIG. 6 illustrating the top, front and left side of the sampler.

A ULD container 70 is illustrated in FIG. 5. Air is being drawn from the illustrated container 70 by a high volume vacuum sampler unit 42. The vacuum sampler unit 42 is coupled to the container 70 by a heavy duty hose 44, which creates a substantially air-tight coupling between the vacuum sampler unit 42 and the container 70.

The air drawn from the container is screened for the presence of prohibited substances using a chemical filter of the same or similar configuration to the sampling card 38 illustrated in FIG. 4. The filter is retained adjacent the container 70 in the illustrated embodiment by a sampling card holder 36. The sampling card holder 36 has a slot in its upper surface that removably receives the sampling card 38.

The sampling card holder 36, sampling card 38, and one end of the hose 44 may be inserted into the ULD container 70 to enable air within the container to be drawn out. The sampling card holder 36 may be inserted via either a flapper door 72, provided at one end of the container, or a side door 74.

During operation, when it is desired to screen a container 70 for prohibited substances, a sampling card 38 is inserted into the slot of the sampling card holder 36 and the vacuum sampler unit 42 is turned on for a sampling interval selected to suit the size and configuration of the container 70 being sampled. Typically the sampling interval is in the range of from about 2 to about 5 minutes. The vacuum sampler unit 42 once turned on draws air out of the container 70 at a high rate, generally equal to about 1,300 liters/min. This high volume sampling rate has been found to provide relatively strong air movement inside the container 70. Air entering the sampling card holder 36 passes across the coated substrate 50 of the sampling card 38 before entering the hose 44 via the outlet port 40.

As the air that is drawn from the freight cargo container passes across the coated substrate 50 of the sampling card 38, localized vapors and airborne particles within the air are entrapped by the adsorbent/absorbent materials coating the substrate 50 of the sampling card 38.

When the sampling interval expires, the vacuum sampler unit 42 shuts off. The sampling card 38 is then manually removed from the slot of the sampling card holder 36 via the handle 52 and is inserted into an analyzer 60, which may be portable. The analyzer 60 in turn heats the sampling card 38 to evaporate entrapped vapors and release entrapped particles and rapidly analyses the vapors and particles (e.g. within 10-30 seconds) to detect the presence of prohibited substances. The analyzer 60 may, for example, be a chromatographic analyzer, a mass spectrometer (stationary or portable), chemiluminescent detector, an axial ion mobility spectrometer (IMS), a field asymmetric ion mobility spectrometry (FAIMS) or a differential mobility spectrometer (DMS).

Research indicates that the expected concentration of threat substances inside ULD containers 70 is likely to be in the parts per trillion levels and that the size of airborne particles of threat substance is likely to be in the range of from about 1 to about 150 micrometers. Given these expected concentration levels and particle sizes, in order to ensure that containers are adequately screened for the presence of prohibited substances, a high volume sampling rate sufficient to ensure good air flow within the freight cargo containers is required. As mentioned above, a high volume sampling rate of about 1,300 liters/min has been found to be acceptable. The sampling interval that is selected during screening is a function of the internal volume of the freight cargo container being screened.

Table 3 shows the percentage volume of air sampled from various empty freight cargo containers during different sampling intervals at a high volume sampling rate of about 1,300 liters/min.

TABLE 3

Percentage volume of air sampled
from various empty ULD containers

| Sampling interval (min) | LD-4 air freight cargo container | LD-7 air freight cargo container |
| --- | --- | --- |
| 2 | 52% | 25% |
| 5 | >100% | 62% |
| 10 | >100% | >100% |
| 15 | >100% | >100% |

Localized Screening System

A handheld portable sampler 100 is illustrated in FIGS. 6 to 9. The sampler 100 functions by drawing gases, vapors and small particles from a localized area through a suitable filter medium which entraps target substances. A vacuum source (preferably a vacuum pump) disposed within the sampler body 105 creates a pressure differential (suction) across the filter, drawing a sample from the targeted area into the sampler body 105. The sampler 100 is configured to draw samples from fabrics (such as a person's clothing, an aircraft seat and hand baggage), surfaces (such as baggage conveyors, the soles of shoes and basins) and small enclosures (such as luggage, aircraft cabin storage lockers and mail bags).

The sampler 100 broadens the screening capabilities of aircraft staff by facilitating targeted localized sampling of passenger, luggage and confined spaces on an aircraft. The sampler 100 is preferably lightweight and compact so that it can be maneuvered into restricted spaces. The illustrated sampler 100, for example, is about 20 cm high by about 11 cm wide and about 22.0 cm thick and only about 2 kg in weight (or 1.5 kg without the interchangeable battery 104), allowing it to be easily maneuvered in constrained spaces, such as within the overhead luggage compartments commonly encountered on commercial aircraft.

The illustrated sampler 100 can be transported and maneuvered by a handle 112 connected to and disposed above the sampler body 105. The vacuum source is activated by depressing a toggle switch 106 disposed at the front end of the handle 112 adjacent the front of the sampler 100. The vacuum source is powered by a battery 104. The illustrated battery 104 is interchangeable, allowing it to be replaced after being discharged to reduce screening disruption.

When the sampler 100 is activated, gas is drawn into the body 105 of the sampler 100 through an inlet nozzle 102. The nozzle 102 extends outwardly in front of the sampler body 105 in the illustrated embodiment. A filter housing 120 is disposed adjacent the rearward end of the nozzle 102. The illustrated nozzle 102 and filter housing 120 are coupled to the sampler body 105 by a hinge 122. A clip 124 secures the filter housing 120 in position between the sampler body 105 and the nozzle 102 when the hinge is closed (as in FIGS. 6, 7 and 9).

The nozzle 102 defines a lumen that extends between the filter housing 120 and an open end of the nozzle 102. The open end of the nozzle 102 is configured to accept various adaptors and sampling probes, allowing the sampler to penetrate rubber gaskets, boxes and allow operator to sample vehicles, enclosures and hard to get areas, including porous surfaces. Gases, vapors and small particles are drawn in through the open end of the nozzle 102 and directed through the filter housing 120 during sampling. The illustrated filter housing 120 is capable of receiving various different filter configurations. One compatible filter 118 is shown inserted into the filter housing 120 in FIG. 9. Filters include a filter medium comprising a substrate coated with an adsorbent/absorbent material.

Figure 9:
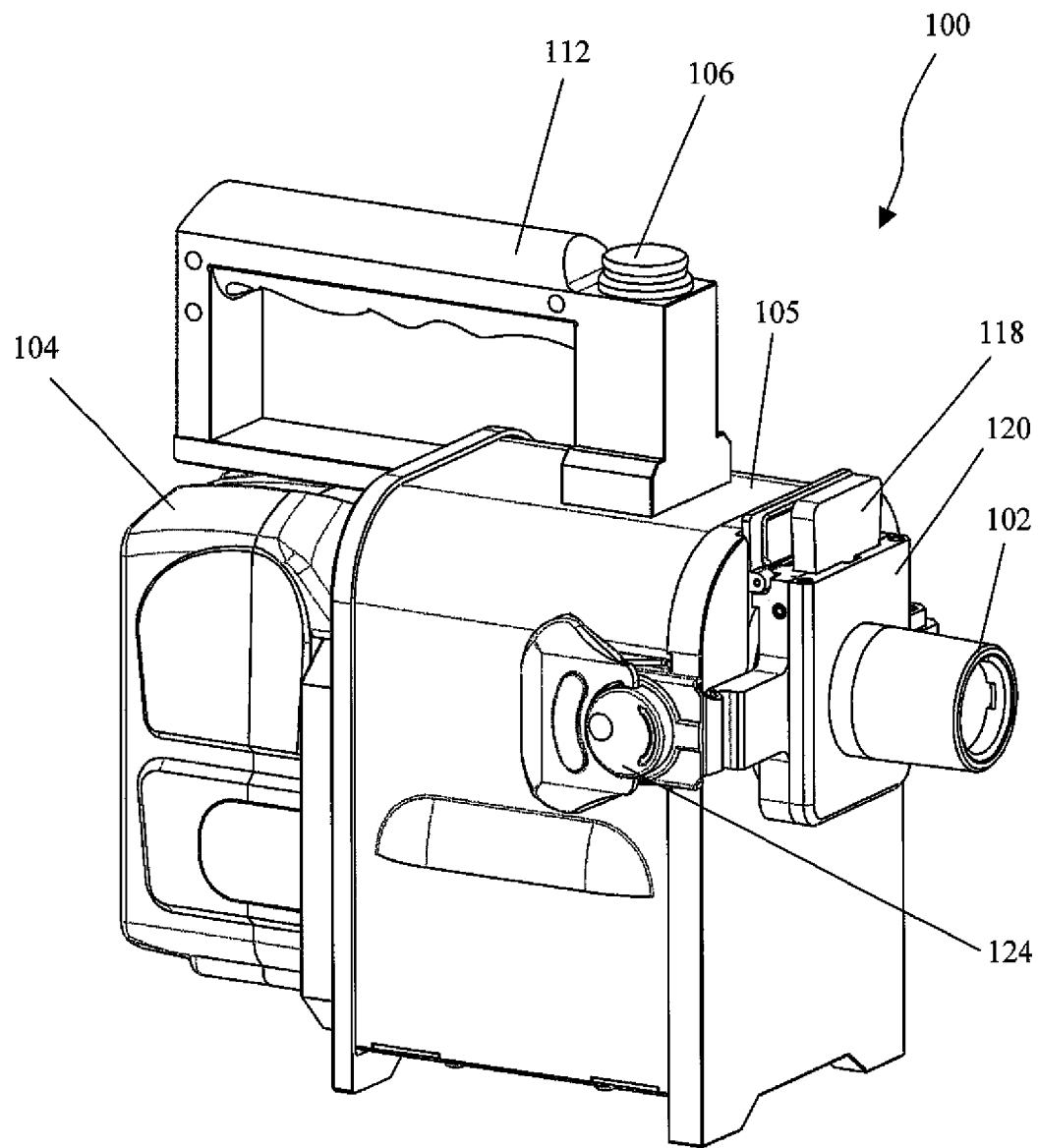
FIG. 9 is a perspective view of the handheld sampler of FIG. 6 illustrating the top, front and right side of the sampler; a filter card is illustrated within the sampler housing in a card holder positioned adjacent the base of the nozzle, the filter card handle projects upwardly from the sampler housing.

A cartridge filter 118, similar to the sampler card 38, is illustrated in FIG. 9 with the handle portion (corresponding to item 52 of sampler card 38) partly visible and the coated substrate portion (corresponding to item 50 of sampler card 38) disposed within the filter housing 120. The cartridge filter 118 comprises a supported filter medium. A frame extends around the filter medium and a handle extends from the frame. The handle facilitates insertion and removal of the filter from a card slot in the filter housing 120.

Unrestrained filters comprising unsupported filter media may alternatively be used. Such filters are secured between the filter housing 120 and the sampler body 105, instead of within the card holder provided for cartridge filters. The filter is partially restrained on the face of the sampler body 105 by an outer positioning lip. The lip may encircle the filter, holding it in place and ensuring the filter is adequately positioned so that it is clamped between the sampler body 105 and filter housing 120 when the hinged filter housing 120 is closed.

Figure 8:
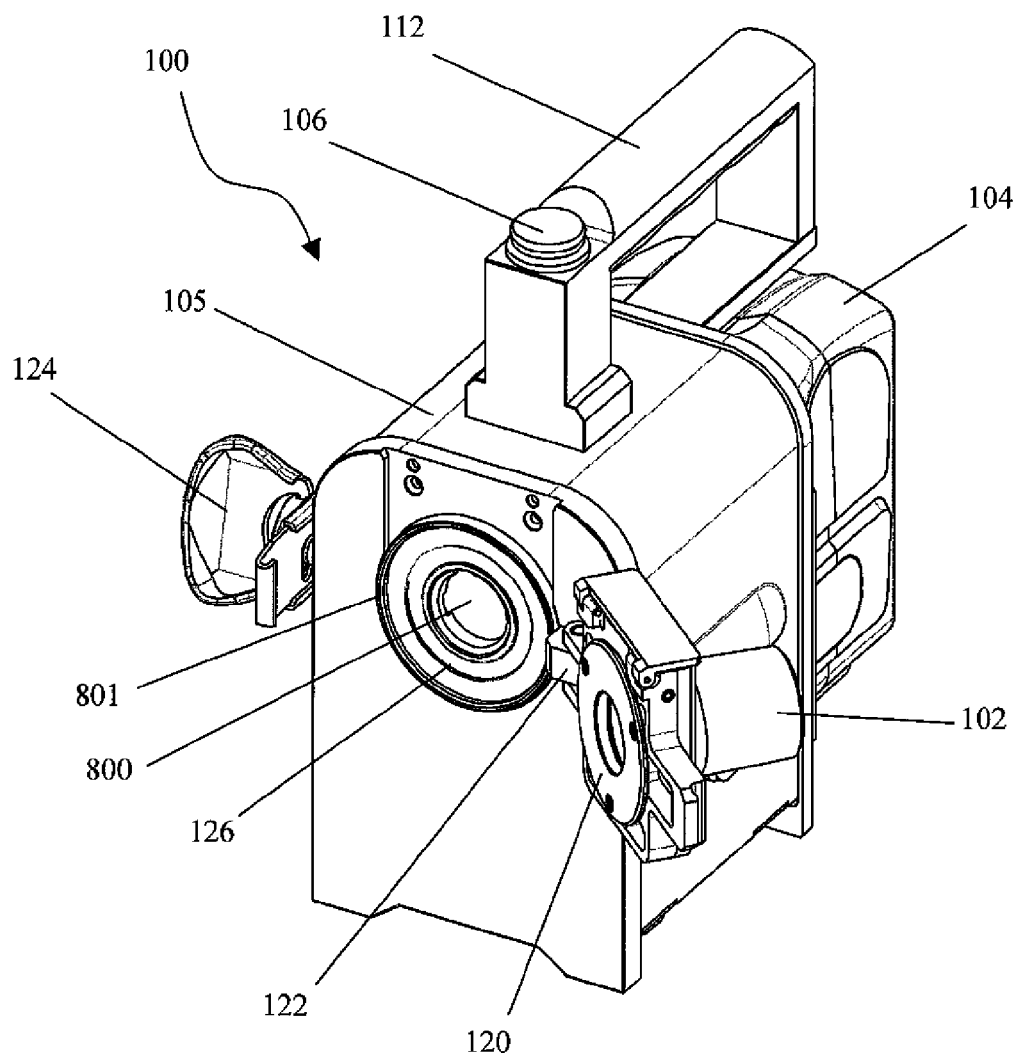
FIG. 8 is a perspective view of the handheld sampler of FIG. 6 illustrating the top, front and left side of the sampler with the hinged filter housing open to reveal the inlet ducting of the filter body.

The sampler 100 is illustrated in FIG. 8 with the hinged filter housing 120 open to reveal the inlet ducting 800 of the filter body 105. A sealing ring 126 is disposed about the inlet ducting, within a space defined by the outer positioning lip 801. The sealing ring 126 is compressed when the hinged filer housing 120 is closed, creating a seal with the filter housing 120. When a large area filter is disposed over the sealing ring, the sealing ring presses the filter against the filter housing 120, sufficiently compressing the filter to create seal the sampler 100. A second positioning lip (not shown), configured to receive smaller unsupported filters, may be disposed within the sealing ring 126.

The sampler 100 preferably utilizes a high flow rate vacuum pump to create suction at the inlet nozzle 102. Higher flow rates allow the sampler 100 to acquire minute particles residing on surfaces or airborne particle floating in the air. Typical flow rates for the illustrated portable sampler are documented in Table 4.

TABLE 4

Typical air flow rates for a portable sampler

| Filter type | Flow rate (L/min) |
| --- | --- |
| No filter | 175-200 |
| Cartridge filter | 125-150 |
| 50 mm diameter unsupported filter | 100 |
| 30 mm diameter unsupported filter | 110 |

A blower port (not shown) is disposed in the bottom surface of the sampler 100. The blower port is configured to concentrate sampled gases being discharged from the sampler 100 into a discharge stream. The discharged gas stream expelled from the blower port can be used to stir air across a targeted surface and displace particles on the surface into the air adjacent the sampler 100. The disturbed air is then drawn into the sampler 100, increasing the probability of detecting any targeted substances on the surface. Disturbing the air over a localized surface can be especially effective for detecting non-volatile substances like cocaine, heroin and plastic explosives.

Sampled gases may also be discharged through a discharge vent 108 in the side of the sampler 100. Preferably, sampled gases are diverted (either in part or entirely) to the discharge vent 108 when a concentrated outlet stream is not required.

Comprehensive Sample Screening

The portable sampler 100 may be used in conjunction with environment sampling and ULD sampling to screen passengers and luggage on an aircraft. Conventional airport passenger and luggage screening (such as metal detection, imaging and random passenger/luggage checks) may also be used.

Comprehensive sample screening methods (incorporating aspects of environment sampling, ULD sampling and portable passenger sampling) generally begin with ULD sampling, as passenger check-in luggage and other cargo is commonly loaded into air freight containers (such as ULD containers) in advance of passenger boarding. Once the luggage is loaded into an air freight container, a sample is drawn from the container before the container is loaded into an aircraft. The sample is generally drawn using suction, which may be generated from a vacuum pump or similar suction source. The sample is passed through a chemical filter which is configured to retained evidence of any target substances contained in the sample. The chemical filter is then analyzed to detect the presence of a target substance within the container.

Personal passenger screening is generally conducted during boarding. Passengers and their carry-on luggage may be screened at the departure gate or on the aircraft. Passenger sampling generally involves drawing a sample from individual passengers clothing and/or hand luggage using a portable sampler. The sample is preferably drawn using suction from a vacuum pump or similar suction source. The sample is passed through a chemical filter that is configured to retain trace evidence of target substances for analysis (similarly to the ULD sample), and the filter analyzed to detect the presence of a target substance within the container.

Finally, once the passengers and/or cargo are loaded into the aircraft, environment samples may be collected. Aircraft environment samples are commonly collected last, after the aircraft has been loaded and suitable air circulation is established within the aircraft. The air within the aircraft is circulated so that it is in contact with passengers before being expelled. The expelled air is sampled, generally over one or more air exchange cycles, by diverting a portion of the expelled air through a chemical filter that is configured to retained evidence of a target substance. The filter is then analyzed to detect the presence of a target substance within the aircraft.

Aircraft environment sampling and individual passenger sampling may also be conducted at the end of a journey to detect narcotics and other prohibited substances. The aircraft cabin, particularly seats, overhead storage lockers and other confined spaces, may also be sampled to detect prohibited substances that have been present during the flight or remain onboard an aircraft.

Post-flight passenger screening generally involves unloading passengers from an aircraft before using a portable sampler to draw a sample from within the aircraft. The samples are passed through a chemical filter, configured to retained evidence of a target substance, and the filter analyzed to detect the presence of a target substance within the aircraft. Preferably sampling and analysis is conducted before passenger's clear customs to allow any suspected passengers to be detained within the airport.

It should be understood that the above-described embodiments of the present invention, particularly, any "preferred" embodiments, are only examples of implementations, merely set forth for a clear understanding of the principles of the invention. Many variations and modifications may be made to the above-described embodiment(s) of the invention as will be evident to those skilled in the art.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The words "comprises" and "comprising", when used in this specification and the claims, are to used to specify the presence of stated features, elements, integers, steps or components, and do not preclude, nor imply the necessity for, the presence or addition of one or more other features, elements, integers, steps, components or groups thereof.

Nothing in this specification or the claims that follow is to be construed as a promise.

The scope of the claims that follow is not limited by the embodiments set forth in the description. The claims should be given the broadest purposive construction consistent with the description as a whole.

What is claimed is:

1. A system for screening aircraft passengers or cargo comprising:
   a sampling probe assembly;
   a sampling card comprising a substrate coated with filtering material, the filtering material being configured to retain vapors and particles of a target substance;
   a sampler housing configured to house the sampler card,
   wherein the sampling probe assembly is configured to either (i) divert a portion of the air expelled b an aircraft air circulation system through the sampler housing so that the sampling card is exposed to the diverted air, (ii) draw a sample from a cargo container using suction before the container is loaded into the aircraft so that the sampling card is exposed to the sample, or (iii) draw a sample from a passenger's clothing or hand luggage using suction prior to the passenger boarding the aircraft so that the sampling card is exposed to the sample,
   wherein the filtering material includes at least two materials selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene.

2. The system of claim 1, wherein the sampling probe assembly is configured to divert a portion of the air expelled by an aircraft air circulation system via an outlet on the exterior of the aircraft through the sampler housing so that the sampling card is exposed to the diverted air.

3. The system of claim 1, wherein the system further comprises an analysis module to analyze the sampling card after it is exposed to the sample or the diverted portion of air to detect the presence of the target substance.

4. The system of claim 1, wherein the filtering material is selected to absorb/adsorb the target substance, the filtering material being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene.

5. The system of claim 1, wherein the coating materials include at least three materials being selected from the group consisting of diphenylene oxide polymers prepared in chloroform, a carbon composite material, divinyl benzene, mono-alkyl substituted benzenes, di-alkyl substituted benzene, toluene, xylenes, and ethylbenzene.

6. The system of claim 1, wherein the filtering material includes at least two materials selected from the group consisting of diphenylene oxide polymers prepared in chloroform, a carbon composite material, and divinyl benzene.

* * * * *